United States Patent [19]

Jaekel et al.

[11] Patent Number: 4,749,658
[45] Date of Patent: Jun. 7, 1988

[54] TWO-WAY VALVE FOR BLOOD ANALYZING APPARATUS

[75] Inventors: Robert W. Jaekel, Lindenhurst; Donald J. Verlee, Libertyville; John L. Vcelka, Zion, all of Ill.

[73] Assignee: Abbott Laboratories, North Chicago, Ill.

[21] Appl. No.: 662,851

[22] Filed: Oct. 19, 1984

[51] Int. Cl.⁴ .................. B01L 11/00; F16K 31/126; G01N 1/10
[52] U.S. Cl. ........................... 436/180; 73/863.72; 73/863.86; 137/247.17; 251/354; 422/103; 422/116
[58] Field of Search ........... 422/103, 100, 113; 436/180; 73/864.13, 863.86, 863.72, 863.73; 137/247.17; 251/318, 319, 324, 325, 331, 332, 354

[56] References Cited

U.S. PATENT DOCUMENTS

| | | | |
|---|---|---|---|
| 3,159,176 | 12/1964 | Russell et al. | 137/493.1 |
| 4,458,543 | 7/1984 | Mieth | 73/863.86 |
| 4,599,219 | 7/1986 | Cooper et al. | 422/102 X |

OTHER PUBLICATIONS

Vernay Laboratories, Inc. 1982 Combination Valves Data Sheets (2 pages).

*Primary Examiner*—Barry S. Richman
*Assistant Examiner*—Jill Johnston
*Attorney, Agent, or Firm*—Willian Brinks Olds Hofer Gilson & Lione, Ltd.

[57] ABSTRACT

Apparatus and method for analyzing a biological material such as blood serum to determine whether a substance indicative of disease is present. The apparatus utilizes a two-way valve construction for rinsing a cartridge containing the material under analysis at various operating stations.

21 Claims, 3 Drawing Sheets

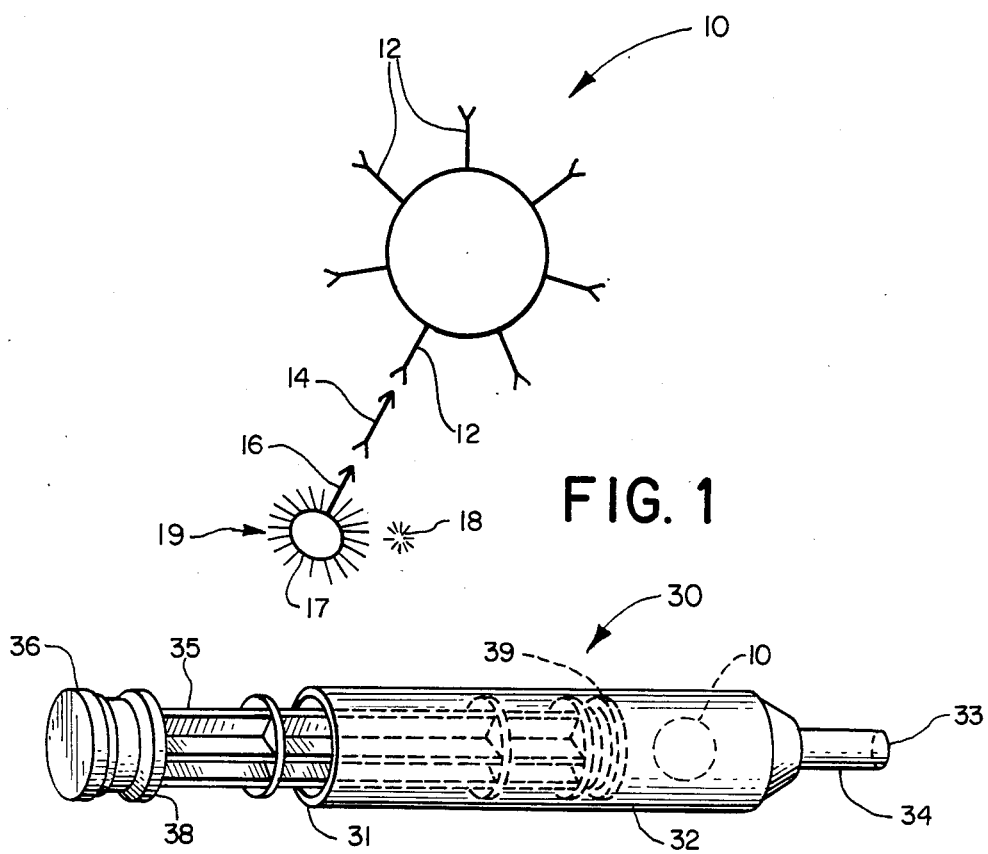
FIG. 1
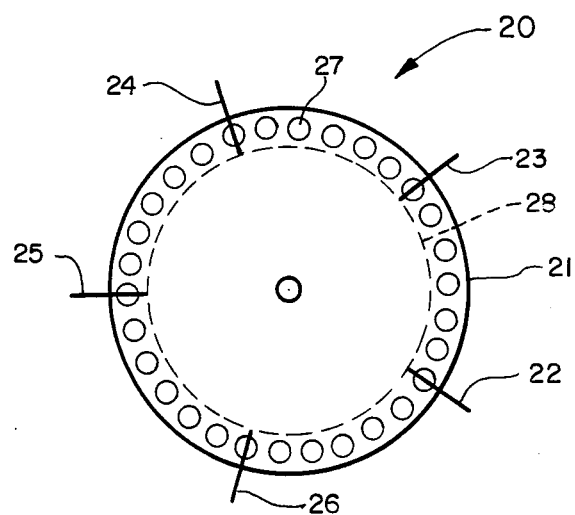
FIG. 2
FIG. 3

TWO-WAY VALVE FOR BLOOD ANALYZING APPARATUS

BACKGROUND OF THE INVENTION

This invention generally relates to apparatus and methods for analyzing a biological material to ascertain whether a particular substance is present or absent. Most particularly, this invention relates to such apparatus and methods wherein the biological material is preferably human blood serum and the substance whose presence or absence is to be determined is preferably a composition indicative of disease, commonly referred to as an antigen. For example, in one aspect of this invention, human blood serum is analyzed to determine whether a hepatitis B surface antigen is present or absent.

Apparatus and methods for analyzing blood serum to ascertain whether a disease is present are especially important in situations where blood is donated by members of the public for the purpose of being subsequently administered to others by transfusion. In such cases it is necessary to analyze the donated blood to ensure that it is free from disease, lest the future user unknowingly contract that disease as a result of such transfusion. The disease for which analysis is most frequently conducted is hepatitis, though other diseases, including AIDS, may also be the subject of such analysis. Thus, though the descriptions referred to herein may specifically refer to hepatitis, it should be understood that such disease is exemplary rather than limitative, the scope of the invention being defined by the appended claims.

In one desirable apparatus for analyzing blood serum for substances indicative of disease, a rotatable incubation wheel is provided for moving a multiplicity of blood serum-containing cartridges to a plurality of operating stations. Such cartridges typically include a plunger, longitudinally movable through a cylindrical cavity containing the blood sample to be analyzed. A polystyrene bead coated with a disease specific antibody or antigen, is ordinarily placed inside the cylindrical cavity of the cartridge, where it can be contacted by a quantity of blood serum subsequently placed therein. As explained hereinafter, as the multiplicity of cartridges are moved by the incubation wheel through the various operating stations, various substances are introduced into the cartridge cavity where they are brought into contact with the antibody-coated or antigen coated polystyrene bead. Depending on the nature of the substances so introduced, and whether the blood serum contains a substance characteristic of the disease that is the object of the analysis then being undertaken, the contents of the cavity may be assayed to provide a "positive" or "negative" indication of that disease.

Though blood analyzing apparatus and methods of the type described have been successfully employed, they are not without certain drawbacks and deficiencies. Accordingly, it is a primary object of this invention to provide improved apparatus and methods for determining whether a particular quantity of blood serum is characterized by a substance indicative of a particular disease. It is another object of the invention to accomplish the foregoing, at least in part, by providing an improved two-way valve structure which permits the material under analysis, and various substances applied thereto, to be evacuated from a cartridge in a reliable, hands-free operation. A further object of the invention is to provide such a two-way valve structure which permits the cartridge to be rapidly and effectively rinsed. It is yet another object of this invention to provide such apparatus and methods which minimize the contamination of the fluid used to rinse the cartridge prior to rinsing.

SUMMARY OF THE INVENTION

The foregoing objects of the invention, along with numerous features and advantages, are achieved in an apparatus for analyzing material utilizing a cartridge, having a body portion containing fluid and a coated bead, and a tip portion. A two-way valve structure is utilized in such apparatus comprising a first valve adapted to pass wash fluid, and a second valve adapted to pass waste fluid. Means, associated with the valve structure, define a first passage communicating with the first valve, and a second passage communicating with the second valve. Receiving means, communicating with the first and second valves, are adapted to receive fluid from, and pass fluid to, the body portion of the cartridge so that the wash fluid, when passing from the first valve to the second valve, contacts the waste fluid only inside the body of the cartridge.

In another aspect of the invention there is provided, in an apparatus for analyzing a material using a cartridge having a body portion containing fluid and a coated bead, and a tip portion, a method for removing fluid from the cartridge and washing the cartridge after fluid has been removed. The method comprises the following steps: engaging the tip portion of the cartridge with a valve construction having first and second valves, and first and second passages communicating, respectively, with the first and second valves; passing wash fluid from the first passage, through the first valve, into contact with the tip portion of the cartridge, through the second valve and into the second passage; ejecting fluid then in the body portion of the cartridge out of the tip portion, through the second valve and into the second passage of the cartridge; and passing wash fluid from the first passage, through the first valve and into both the tip portion and the body portion of the cartridge.

BRIEF DESCRIPTION OF THE DRAWINGS

An exemplary embodiment of the invention summarized above is shown in the accompanying drawings wherein:

FIG. 1 is a schematic representation of a bead, and the various substances adhering thereto, preferably used in connection with carrying out the present invention;

FIG. 2 is a schematic view of a cartridge containing the bead shown in FIG. 1, said cartridge being representative of the type used in connection with the present invention;

FIG. 3 is a very simplified schematic representation of apparatus of the type used in carrying out the present invention, said apparatus being adapted to carry a multiplicity of cartridges of the type shown in FIG. 2;

DETAILED DESCRIPTION OF AN EXEMPLARY EMBODIMENT OF THE INVENTION

Figure 4:
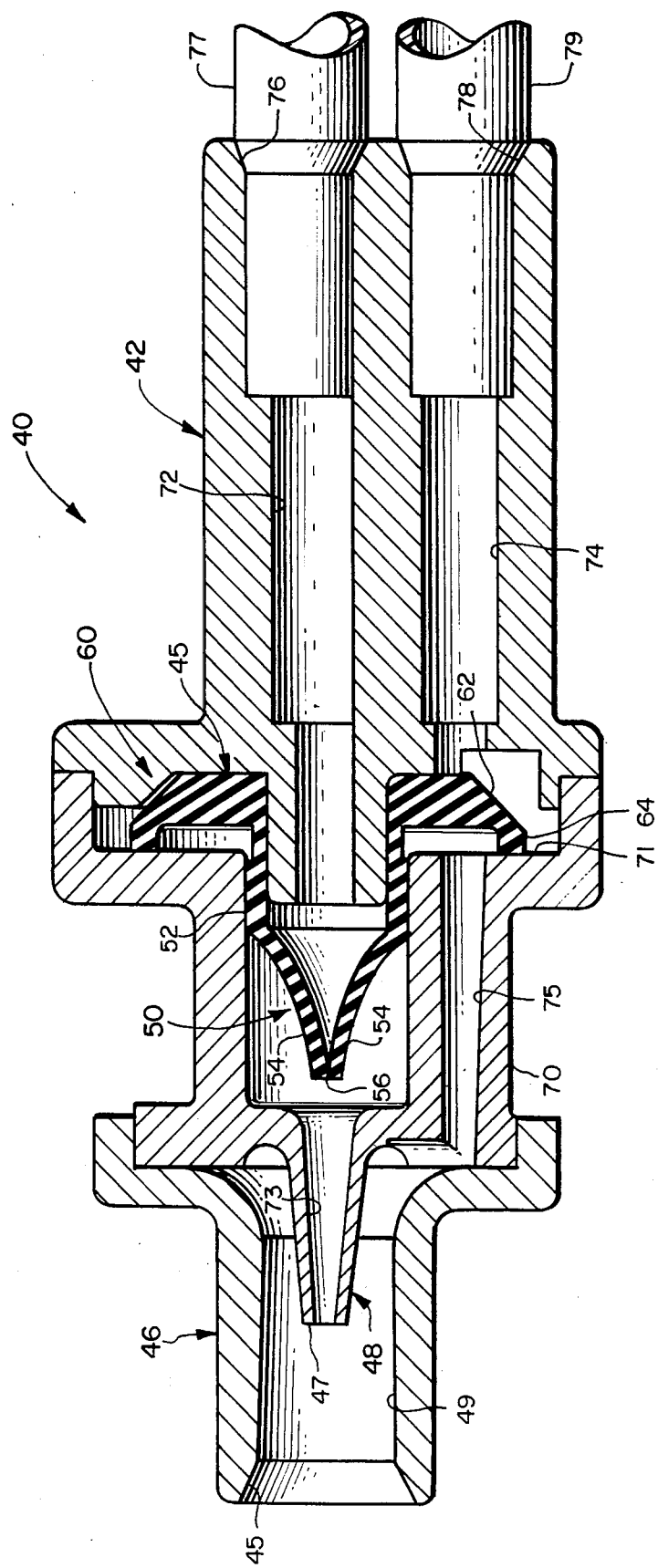
FIG. 4 is a two-way valve structure operative as part of the apparatus shown in FIG. 3, and being representative of a preferred embodiment of the invention.

As explained hereinbefore, the present invention pertains to apparatus and methods for analyzing biological material to determine whether a particular substance is present or absent. In a preferred form of the invention, the biological material to be analyzed is human blood serum, and the substance whose presence or absence is to be determined is a composition associated with the blood serum indicative of disease. Such composition usually contains a protein or carbohydrate which, when introduced into the body, stimulates the production of an antibody. The specific protein or carbohydrate composition which incites antibody production is commonly referred to as an antigen.

For exemplary purposes only, the detailed description that follows explains the apparatus and methods in terms of analyzing a quantity of human blood serum for purposes of determining whether that blood serum has a substance indicative of hepatitis, i.e., the blood serum is analyzed to determine whether an antigen corresponding to surface B hepatitis is present. It should be clearly understood, however, that the present invention is not so limited, but is also useful in analyzing blood serum to determine whether other substances, indicative of other diseases, may be present, in analyzing other biological fluids such as saliva, urine, throat swabs and the like, or in other applications not specifically described.

The present invention is preferably carried out by using means to which various substances are applied for purposes of conducting an analysis of a biological material such as human blood serum. As shown in FIG. 1, such means preferably take the form of a small bead 10, typically formed from polystyrene or some similar material, and typically being on the order of about ¼ inch in diameter. In accordance with well-known procedures, bead 10 is coated with an antibody specific to the particular disease that will be the subject of analysis. If this disease is hepatitis, for example, bead 10 will be coated with a hepatitis B surface antibody 12, represented diagrammatically by a plurality of inverted arrows, disposed about the periphery of bead 10. If another disease, such as AIDS, is the subject of analysis, bead 10 will, of course, be coated with a different antibody or AIDS specific agent.

In accordance with well-known and well-understood biological phenomenon which need not be described in detail herein an antibody for a particular disease will bond to the antigen corresponding to that disease when the antibody and the antigen are brought into contact under suitable conditions. Thus, if proper temperature and time parameters exist, a hepatitis B surface antigen 14, brought into contact with the antibody 12 to hepatitis B surface antigen 14 covering bead 10, will become bonded thereto. Similarly, an antibody 16 conjugated with an enzyme marker 17 to provide antibody-enzyme conjugate 19, may become bonded to antigen 14 under proper time and temperature conditions. Antigen 14 and antibody-enzyme conjugate 19 are shown in diagrammatic form in FIG. 1.

Certain color-developing substances, commonly known as chromophores and represented diagrammatically at 18 in FIG. 1 are known to change color in the presence of certain materials. One such chromophore is tetramethylbenzidine. When the enzyme marker is horse radish peroxidase, tetramethylbenzidine in a mixture including peroxide can be used to provide an indication that the hepatitis B surface antigen is present. The presence of this particular antigen in the blood serum under analysis is, of course, indicative of a "positive" test for hepatitis.

Bead 10, coated with appropriate antibody 12 is deposited in a laboratory cartridge 30 of the type shown in FIG. 2. Cartridge 30 has a body portion 37 defining a substantially cylindrical cavity 32 having a distal opening 31. At its proximal end body portion 37 tapers to a tip portion 34 terminating in a proximal opening 33. In this exemplary embodiment, bead 10, coated with antibody 12, is deposited in cavity 32 before analysis begins.

Cartridge 30 further includes a plunger 35 having a distal handle 36 formed with a flange 38 to assist in actuation of the plunger. Associated with plunger 35 is at least one sealing ring 39 which serves as a barrier to fluid in cavity 32, and which aids in forcing such fluid through tip 34 and out proximal opening 33 when plunger 35 is urged through cavity 32.

Initially, plunger 35 is retracted from cavity 32 so that bead 10, coated with antibody 12, can be put into cavity 32 via distal opening 31. Means (not shown) may then be used to draw a quantity of material, such as blood serum, into cavity 32 of cartridge 30, permitting that material to contact the antibody-coated bead 10. Alternatively, pipetting may be used so that the material to be analyzed will not enter cavity 32 until a timed operation is about to commence. This enables one to accurately control the time in which the material is in contact with the antibody 12 on bead 10.

Cartridge 30, containing both the material to be analyzed and the bead 10, may then be loaded on an apparatus of the type represented schematically by apparatus 20 in FIG. 3. Apparatus 20 incudes a rotating incubation wheel 21 having a plurality of cartridge receiving cavities 27 and an incubation heater strip schematically illustrated at 28. Apparatus 20 further includes a plurality of operating stations identified by reference numerals 22–26. Operating station 22 represents a load station where cartridges containing the material to be analyzed and the bead 10 are sequentially loaded onto wheel 21. For exemplary purposes, the material to be analyzed is referred to hereinafter as blood serum.

After cartridge 30 has been loaded onto incubation wheel 21, and the blood serum is brought into contact with antibody-coated bead 10, wheel 21 is preferably rotated for approximately 37 minutes while subjecting cartridge 30 to temperatures of about 40° C. It has been found that these parameters of time and temperature represent a sufficient incubation period for any hepatitis B surface antigen associated with the blood serum in cavity 31 of cartridge 30 to bond to the antibody 12 coated on bead 10. Thus, if the blood serum in cartridge 30 is infected with hepatitis, hepatitis B surface antigen will be present, and it will become bonded to the hepatitis antibody coated bead 10 after the incubation period has been concluded. On the other hand, if the blood serum in cartridge 30 is not infected with hepatitis, there will be no hepatitis B surface antigen present in the blood serum, and therefore no such antigen will be available for bonding to the antibody-coated surface of bead 10.

After cartridge 30 has been rotated by wheel 21 for a period of time sufficient to cause any hepatitis antigen associated with the blood serum contained in cavity 32 to become bonded to the antibody-coated surface of bead 10, the apparatus 20 causes wheel 21 to stop at operating station 23. At operating station 23, the excess blood serum is discharged from cavity 32, the cavity is washed, and then the contents, i.e., bead 10 with antibody 12 and antigen 14 successively bonded thereto, is exposed to antibody-enzyme conjugate 19. In this exemplary embodiment enzyme marker 17 is a specific compound known as horse radish peroxidase. Being hepatitis specific, antibody 16 (and enzyme marker 17) bonds to antigen 14 for reasons previously explained. In summary, at operating station 23 the portion of the blood serum which did not bond to the antibody-coated bead 10 is first expelled from cavity 32, and the cavity is then washed to remove residue therein. When this washing operation is completed, the antibody-enzyme conjugate 19 is introduced into cavity 32. As explained in greater detail hereinafter, some of the functions performed at operating station 23 are carried out with the use of a novel two-way valve construction 40 described in connection with the discussion of FIG. 4.

After antibody-enzyme conjugate 19 has been introduced into cavity 32, wheel 21 is again operated, causing cartridge 30 to be rotated for about 15 minutes at a temperature of approximately 40° C. until the reaction is complete. When this second incubation period is completed, wheel 21 stops at operating station 24 where another washing cycle is undertaken to remove all conjugate and enzyme material from cavity 32 which did not bond to the bead 10 during the second incubation process. When the unbonded material is removed, the color-developing chromophore mixture is introduced into cavity 32. This chromophore mixture preferably includes the chromophore tetramethylbenzidine mixed with peroxide. Tetramethylbenzidine will turn blue in the presence of peroxide if the enzyme horse radish peroxidase is present. Of course, antibody-enzyme conjugate 19 is present only if bonded to antigen 14; and antigen 14 is present only if the blood serum originally introduced into the cartridge 30 was infected with hepatitis. If the blood serum was not so infected, there would have been no antigen 14 bonded to the antibody-coated bead 10, no conjugate bonded to the antigen 14, and therefore no enzyme 17 to cause chromophore 18 to change color. In short, the changing of chromophore 18 to a blue color is a "positive" indication that the blood serum originally deposited in cavity 32 of cartridge 30 was infected with hepatitis. As explained in greater detail hereinafter, some of the functions performed at operating station 24 are also carried out with the use of two-way valve construction 40.

After the chromophore 18 is introduced, the cartridge 30 is again rotated on wheel 21 for about eight minutes at approximately 40° C. When this final incubation period is completed, wheel 21 is stopped at operating station 25. It is at this operating station where a sample of the chromophore 18, representative of the blood serum originally deposited in cartridge 30, is ejected into a chamber and analyzed by an optical readout device. If the chromophore 18 turned blue as a result of the presence of enzyme 17, the optical readout device will develop a signal indicative of a "positive" hepatitis reaction. The absence of this signal, on the other hand, is indicative of a "negative" hepatitis reaction.

After the chromophore is ejected at operating station 25, and the optical analysis is undertaken, wheel 21 moves cartridge 30 to operating station 26. It is at operating station 26 that cartridge 30 is removed from wheel 21 of apparatus 20. It should be understood that throughout the course of this analysis, other cartridges may be simultaneously loaded, washed, and removed, whereby the results of numerous analyses can be completed during the time any single cartridge is loaded at operating station 22 and subsequently removed from apparatus 20 at operating station 26.

Referring now to FIG. 4, there is shown an exemplary embodiment of the novel two-way valve construction 40. Valve construction 40 comprises a housing 42 preferably formed from clear ABS material. In this exemplary embodiment, housing 42 defines a first interior passage 72 and a second interior passage 74 terminating, respectively, in a first port 76 and a second port 78. Ports 76 and 78 are adapted to receive, respectively, plastic tubes 77 and 79.

Tube 77 may be coupled to a source of wash fluid (not shown) and tube 79 may be coupled to a sink or container for receiving waste fluid (not shown). Tube 79 may further be coupled to means for creating a vacuum for sucking fluid through passage 74 and out second port 79. Such vacuum may be on the order of 10 inches of mercury.

Passages 72 and 74 communicate with valve means 45 which preferably comprise a first valve 50 and a second valve 60. More particularly, valve 50 comprises a body 52 communicating with passage 72. Body 52 terminates in a pair of normally closed lips 54 defining an outlet 56. Valve 50, sometimes referred to herein as a duck bill valve, conventionally passes fluid through body 52 and out outlet 56 when the pressure inside lips 54 is sufficiently greater than the pressure outside lips 54 to allow outlet 56 to open. Thus, when the vacuum applied via tube 79 appears outside lips 54, outlet 56 ordinarily opens.

Valve 60, which is normally closed, comprises a circumferential flange 62 defining a sealing surface 64. When open, valve 60 allows fluid to pass from a channel 75 formed in housing 70 to passage 74, the former communicating with valve 50. Valve 60 is sometimes referred to herein as an umbrella valve. Valve 50 and valve 60 are preferably formed as a single piece part, such part being available, for example, from Vernay Laboratories, Inc. under catalog no. VA3813.

Two-way valve mechanism 40 further includes tapered means 48 defining a communication 73 aligned with outlet 56 of first valve 50. Tapered means 48 terminates in an orifice 47 which opens into receiving means 46 defined by housing means 42. Receiving means 46 has an interior space 49 terminating in a tapered orifice 51 (see FIGS. 4A–4D) adapted to receive the tip portion 34 of cartridge 30 when cartridge 30 is at operating stations 23 and 24 of apparatus 20 (FIG. 3).

At operating station 23, for example, cartridge 30, containing a quantity of blood serum and an antibody-coated bead 10, is docked in apparatus 20. As previously described, excess blood serum is then ejected from cartridge 30, whereupon cartridge 30 is washed and filled with a quantity of conjugate. At operating station 24, on the other hand, the excess conjugate is removed, whereupon cartridge 30 is washed and filled with a quantity of chromophore.

Figures 4A, 4B, 4C, 4D:
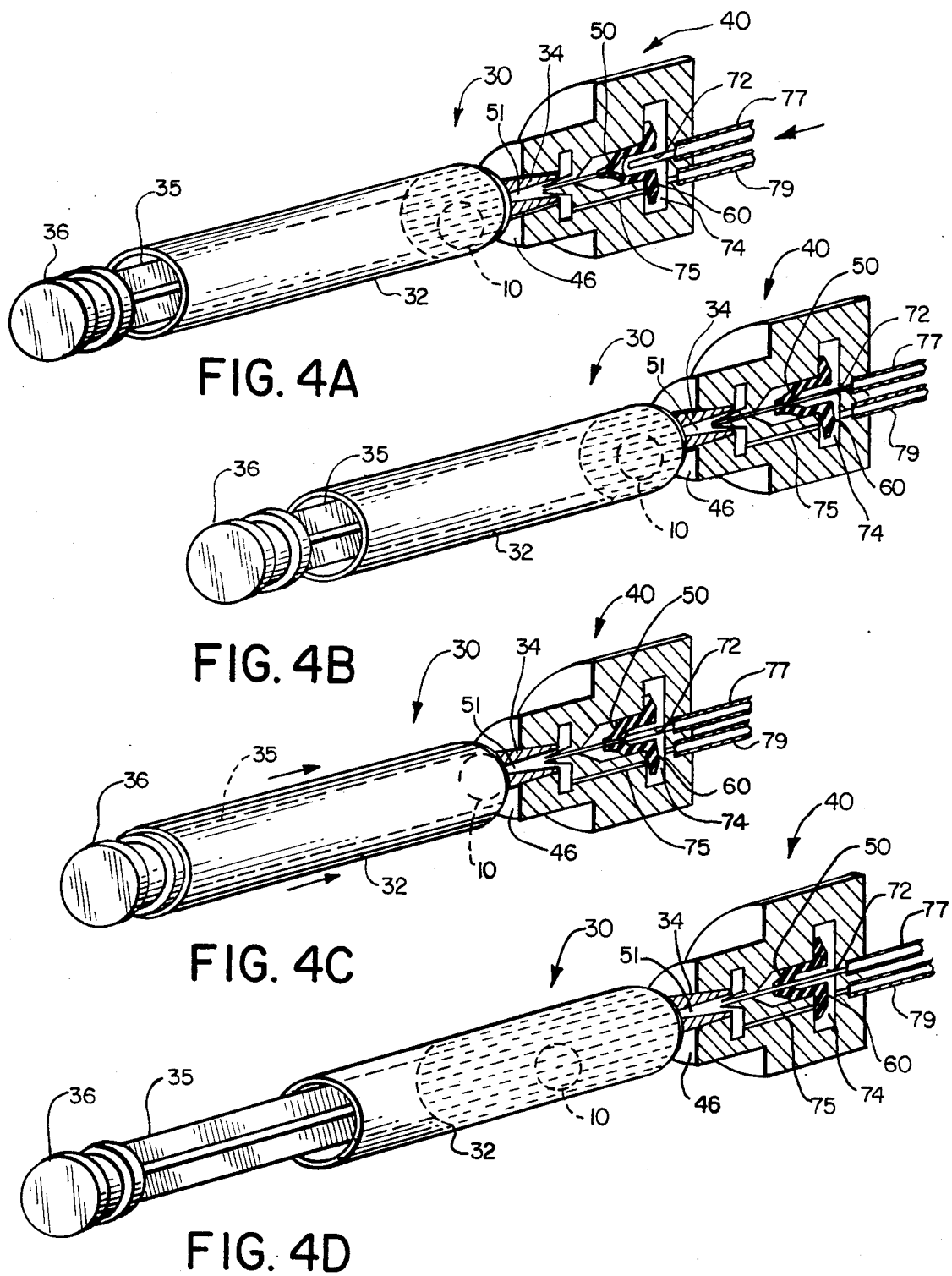
FIGS. 4A-4D represent a schematic view, partially cut-a-way, of a portion of the two-way valve structure shown in FIG. 4 in four different operative positions with respect to the cartridge shown in FIG. 2.

The sequence in which these functions at operating stations 23 and 24 occur is shown diagrammatically in FIGS. 4A–4D. Referring first to FIG. 4A, tip portion 34 of cartridge 30 is inserted into receiving means 46 of two-way valve mechanism 40, with tube 77 being coupled to a source of wash fluid and tube 79 being coupled to a sink for waste fluid. As previously explained, tube 79 is also coupled to a vacuum, first valve 50 is normally closed and second valve 60 is normally open.

Before tip portion 34 is sealed against the inner walls of receiving means 46, the vacuum to which tube 79 is coupled causes air to pass from outside cartridge 30, around the outside of tip portion 34 and into receiving means 46. This air flow dries off the tip portion 34, and otherwise serves to dry impurities that may have adhered thereto. This step minimizes the risk of cross contamination from cartridge to cartridge at the wash station.

As cartridge 30 is inserted further into receiving means 46, the outer portion of tip portion 34 becomes sealed against the inner walls of receiving means 46, thereby blocking the air path previously described. As shown in FIG. 4B, however, the vacuum applied from tube 79 causes outlet 56 to open. When outlet 56 opens, a fluid path is established from first passage 72 through valve 50 and a portion of tip portion 34, to channel 75, second valve 60 and second passage 74. As a result the vacuum applied via tube 79 causes wash fluid, to pass from tube 77 into the tip portion 34 of cartridge 30 thereby removing residue adhering thereto. Waste fluid, comprising the wash fluid and the residue removed from the interior of tip portion 34, is then passed through channel 75, second valve 60 and first passage 74 as a result of the vacuum applied to tube 79.

When the tip portion 34 of cartridge 30 has been washed, cartridge 30 is actuated by pushing distal end 36, causing plunger 35 to eject the contents in body portion 37 out of tip portion 34 and into receiving means 46. When plunger 35 is pushed in the manner so described, a pressure of greater than about 20 inches of mercury is produced, and applied outside first valve 50. This pressure typically exceeds the vacuum from tube 79, thereby causing valve 50 to close. This, in turn, blocks the fluid path from first passage 72 to receiving means 46. The fluid path via receiving means 46, channel 75, second valve 60 and second passage 74 remains open. As a result, the contents ejected from body portion 37 of cartridge 30 passes through second passage 74, via tube 79 to a sink for receiving such waste fluid. After the plunger 35 is pushed in completely, the vacuum again causes valve 50 to open and any waste fluid residue inside the tip portion 34 is washed out as described previously. This step assures that only clean water will be drawn into the body portion 37 of cartridge 30 when the plunger 35 is pulled back.

After the contents of cartridge 30 has been ejected in the manner described, plunger 35 is pulled back as illustrated in FIG. 4D. This produces a vacuum of about 25 inches of mercury which causes valve 50 to reopen and valve 60 to close. As a result, wash fluid is passed from first passage 72, through valve 50 and receiving means 46, into both the tip portion 34 and the body portion 37 of cartridge 30. This wash fluid serves to rinse cartridge 30 of residue material, the mixture becoming a waste fluid.

Immediately after plunger 35 has been pulled back, the vacuum produced by that movement is dissipated, whereby valve 60 reopens. Plunger 35 is then pushed in (FIG. 4C) to eject the combination of wash fluid and residue, i.e., waste fluid, inside cartridge 30. As plunger 35 is pushed, however, the pressure so created closes valve 50, whereby the waste fluid is passed via channel 75, valve 60 and second passage 74, to tube 79. The rinsing of cartridge 30 is preferably repeated 3-5 times to ensure that the original contents of cartridge 30 (except, of course, for the coated bead 10 which is too large to pass through opening 33) is completely expelled or at least, very much diluted. When this occurs, tip portion 34 may be disengaged from receiving means 46. Before tip portion 34 is displaced too far from receiving means 46, however, it is preferred to again dry the outside of tip portion 34 with air in the manner described in connection with the discussion of FIG. 4A.

Throughout this functional sequence it should be realized that the wash fluid passed from tube 77 is ordinarily not contaminated by any residue or waste material until the wash fluid actually rinses that material from cartridge 30. In this way a clean wash fluid is always used for its intended purpose, thereby assuring that cartridge 30 is properly rinsed.

With the excess fluid in cartridge 30 expelled, and both tip portion 34 and body portion 37 repeatedly rinsed to remove any residue, cartridge 30 can then be positioned to receive additional fluid necessary to carry-on the analysis. Thus, in this exemplary embodiment, conjugate will be added to cartridge 32 at operating station 23, and chromophore will be added to cartridge 32 at operating station 24. The cartridge will then be moved to operating station 25 where the analysis can be concluded, and a signal indicative of the presence or absence of hepatitis can be developed.

What has been described is an apparatus and method for carrying on the analysis of a biological material such as blood serum, utilizing a novel two-way valve construction. Although the apparatus and methods disclosed herein are preferred, it is believed that other embodiments which do not part from the true scope of the invention will become apparent to those skilled in the art. Accordingly, all such embodiments are intended to be covered by the appended claims.

We claim:

1. An apparatus for analyzing material comprising:
   a cartridge having a body portion, containing a coated bead, and a tip portion; and
   a two-way valve construction comprising:
   first valve means, adapted to pass a first fluid,
   second valve means, adapted to pass a second fluid;
   housing means, substantially surrounding said first and said second valve means, defining a first passage communicating with said first valve means, and a second passage communicating with said second valve means;
   receiving means, communicating with said first and said second valve means, adapted to receive said cartridge; and
   valve actuation means movable between a first position wherein at least a partial vacuum is generated in said cartridge for substantially simultaneously opening said first valve means and closing said second valve means so that a first fluid is passed from said first passage, through said first valve means, and into both said tip portion and said body portion of said cartridge, and a second position wherein a fluid in said cartridge is pressurized for substantially simultaneously closing said first valve means and opening said second valve means so that a second fluid from the body portion of said cartridge, is passed through said second valve means, into said second passage.

2. The apparatus defined in claim 1 wherein said second valve means comprises flange means adapted to become sealed against an interior surface of said housing means when said second valve means is closed.

3. The apparatus defined in claim 1 wherein said first passage communicates with a tube adapted to be coupled to a source of wash fluid.

4. The apparatus defined in claim 1 wherein said first valve means is a duck bill valve and said second valve means is an umbrella valve.

5. The apparatus defined in claim 2 wherein said duck bill valve and said umbrella valve are integrally formed.

6. The apparatus defined in claim 1 wherein said receiving means defines an interior space conforming to said tip portion of said cartridge.

7. The apparatus defined in claim 4 wherein said valve construction further comprises tapered means disposed between said first valve means and said interior space.

8. The apparatus defined in claim 1 wherein said second passage communicates with a tube adapted to be coupled to a container for waste fluid.

9. The apparatus defined in claim 8 wherein said cartridge includes a plunger, and wherein the pressure in said tube is kept at a pressure substantially lower than atmospheric pressure and substantially higher than the pressure in said cartridge when said plunger is being pulled back in said cartridge.

10. The apparatus defined in claim 1 wherein said valve actuation means includes means coupled to said second passage for applying a pressure lower than atmospheric pressure thereto.

11. The apparatus defined in claim 10 wherein said valve actuation means includes means for sealing the exterior of said tip portion of said cartridge against the interior of said receiving means whereby said pressure lower than atmospheric pressure causes said first valve means to open.

12. A method for removing fluid from an analyzing cartridge having a tip portion, and a body portion containing fluid and a coated bead, comprising the steps of:
(a) engaging said tip portion of the cartridge with a valve construction having first and second valve means and first and second passages communicating, respectively, with said first and second valve means;
(b) ejecting said fluid then in the body portion of the cartridge out of said tip portion, through said second valve means and into said second passage; and
(c) thereafter passing a first fluid through said first passage and said first valve means, and into the tip portion and the body portion of the cartridge.

13. The method defined in claim 12 wherein, after step (a), but before step (b) there is the step of:
passing said first fluid from said first passage, through said first valve means, into contact with the tip portion of said cartridge, through said second valve means and into said second passage.

14. The method defined in claim 12 wherein, prior to the engagement of said cartridge and said valve construction; there is the step of: sucking air from outside the cartridge, around the tip portion thereof, through said second valve means, and into said second passage.

15. The method defined in claim 12 further includes repeating steps (b) and (c).

16. The method defined in claim 15 wherein, after the steps of (b) and (c) are repeated, the step of: disengaging said cartridge from said valve construction and sucking air from outside said cartridge, around the tip portion thereof, through said second valve means and into said second passage.

17. A method for removing fluid from an analyzing cartridge having a tip portion, and a body portion containing fluid and a coated bead, comprising the steps of:
(a) applying a first vacuum through an open second valve means to a normally closed first valve means sufficient to open said first valve means and thereby cause a first fluid to be passed through said first valve means to the tip portion of the cartridge;
(b) actuating the cartridge to eject fluid from the body portion thereof, thereby developing a positive pressure sufficient to close said first valve means, said second valve means remaining open, so that said fluid so ejected is passed from the cartridge through said second valve means; and
(c) actuating the cartridge to draw fluid therein, thereby developing a second vacuum sufficient to open said first valve means and close said second valve means so that said first fluid passes through said first valve means and into the tip portion and the body portion of the cartridge.

18. The method defined in claim 1 wherein, prior to the engagement of said cartridge and said valve construction; there is the step of: sucking air from outside the cartridge, around the tip portion thereof, and through said second valve means.

19. The method defined in claim 20 further includes repeating steps (b) and (c).

20. The method defined in claim 19 wherein, after the steps (b) and (c) are repeated, the step of: disengaging said cartridge from said valve construction and sucking air from outside the cartridge, around the tip portion thereof, and through said second valve means.

21. In an apparatus for analyzing material including a cartridge having a body portion containing a coated bead, a tip portion for passing fluid to and from said body portion, an actuable plunger movable between a first position wherein at least a partial vacuum is generated in said cartridge and a second position wherein at least a partial positive pressure is generated in said cartridge; and means for providing fluid to and receiving fluid from said cartridge, the improvement comprising:
a two-way valve apparatus comprising:
first valve means;
second valve means;
first passage means communicating with said first valve means for passing wash fluid thereto;
second passage means for communicating with said second valve means for applying a first pressure thereto;
said first and said second valve means each being operative to open in response to a value of said first pressure less than atmospheric pressure in the absence of a second pressure developed by the movement of the actuable plunger from said first to said second position; and
receiving means communicating with said first and second valve means and having means for receiving the tip portion of the cartridge for passing wash fluid thereto when said first valve means is opened.

* * * * *

UNITED STATES PATENT AND TRADEMARK OFFICE
CERTIFICATE OF CORRECTION

PATENT NO. : 4,749,658
DATED : June 7, 1988
INVENTOR(S) : Jaekel et al.

It is certified that error appears in the above-identified patent and that said Letters Patent is hereby corrected as shown below:

IN THE CLAIMS

In col. 9, line 55, please delete the first occurrence of "said" and substitute therefor --the--.

In col. 9, line 58, please delete the first occurrence of "said" and substitute therefor --the--.

In col. 10, line 1, please delete the first occurrence of "said" and substitute therefor --the--.

In col. 10, line 25, please delete "1" and substitute therefor --17--.

In col. 10, line 26, please delete the first occurrence of "said" and substitute therefor --the--.

In col. 10, line 30, please delete "20" and substitute therefor --17--.

In col. 10, line 34, please delete the first occurrence of "said" and substitute therefor --the--.

Signed and Sealed this

Seventeenth Day of July, 1990

Attest:

HARRY F. MANBECK, JR.

*Attesting Officer*    *Commissioner of Patents and Trademarks*